United States Patent [19]

Alam et al.

[11] 4,316,884
[45] Feb. 23, 1982

[54] SUSTAINED RELEASE PHARMACEUTICAL FORMULATION

[75] Inventors: Abu S. Alam, Westerville; Herman J. Eichel, Columbus, both of Ohio

[73] Assignee: Adria Laboratories, Inc., Columbus, Ohio

[21] Appl. No.: 160,887

[22] Filed: Jun. 19, 1980

Related U.S. Application Data

[63] Continuation-in-part of Ser. No. 6,971, Jan. 25, 1979, abandoned.

[51] Int. Cl.³ .................................................. A61K 9/50
[52] U.S. Cl. .......................................... 424/19; 424/35
[58] Field of Search .................................... 424/19–22, 424/35

[56] References Cited

U.S. PATENT DOCUMENTS

| | | | |
|---|---|---|---|
| 3,155,590 | 11/1964 | Miller et al. | 424/35 |
| 3,341,416 | 9/1967 | Anderson et al. | 424/35 |
| 3,488,418 | 1/1970 | Holliday et al. | 424/35 |
| 3,922,338 | 11/1975 | Estevenel et al. | 424/21 |

OTHER PUBLICATIONS

Chem. Abstr. 87 #141233m (1977), 86 #150629(b) #8593s (1977), 82 #106135f (1975), 82 #118718m (1975), 80 #10382s (1974).
De Sabata, V. Chem. Abstr. 87 #157026g (1977) of Drugs Pharm. Sci., 1976(3)(Micro-encapsulation), 143–161, "Bioavailability from Microencapsulated Drugs".
Bakan, J. Chem. Abstr. 84 #126673z (1976) of Polym. Sci. Technol., 1975(8) (Polym. Med. Surg.): 213–235, "Microcapsule Drug Delivery Systems".
Chem. Abstracts Index "Capsules", vol. 66 (1967) and vol. 89 (1978) "Microcapsule" entries.

*Primary Examiner*—Shep K. Rose
*Attorney, Agent, or Firm*—Marion C. Staves

[57] ABSTRACT

It has been found that indoprofen can be used in increased safety at its effective anti-inflammatory dose in humans and that the activity of indoprofen is greatly prolonged by microencapsulating microparticles of indoprofen in a solid protective coating of a cellulose ether such as ethylcellulose.

11 Claims, No Drawings

SUSTAINED RELEASE PHARMACEUTICAL FORMULATION

This application is a continuation-in-part of copending application Ser. No. 6,971, filed Jan. 25, 1979, now abandoned.

This invention relates to sustained release pharmaceutical formulations. More particularly this invention relates to microencapsulated indoprofen most preferably in the form of tablets.

Indoprofen is a relatively new and important drug having anti-inflammatory and analgesic properties described in Girraldi et al British Pat. No. 1,344,663 (1974) and various articles, such as Pedronetto et al, The Journal of International Medical Research, Vol. 3, No. 1, pages 16–20 (1975). The drug has the following structural formula

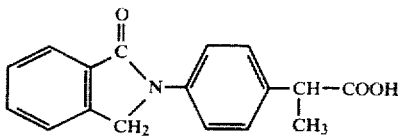

and can be named alpha-[4-(1-oxo-2-isoindolinyl)-phenyl]propionic acid. While indoprofen exhibits excellent anti-inflammatory and analgesic properties, its short plasma half-life (t $\frac{1}{2}$ = 2.1–5.4 hours) in humans is a drawback.

Sustained release forms of medication are known in the art. They provide for prolonged action of a drug in the gastro-intestinal tract by slow release over an extended period of time. One way of achieving sustained release of a drug is the use of a tablet wherein the core containing the active ingredient is surrounded by a layer of inert material, such as an enteric substance which allows the tablet to pass unchanged through the stomach and disintegrate in the intestinal tract. Such enteric coated tablets often suffer from the disadvantage of not providing a uniform and constant drug release.

A recent patent, i.e., U.S. Pat. No. 3,155,590, discloses a process of encapsulating minute aspirin particles with a polymeric wall material that is ingestible in living creatures and prolongs the activity of the aspirin double or triple the time of the unencapsulated drug.

The analgesic dose for indoprofen in man is low in comparison to the anti-inflammatory dose, i.e., in the order of 100 to 600 mg. per day. At this dosage regimen, indoprofen exhibits its maximum analgesic effect and has minimal or negligible side effects.

However, the dose necessary for indoprofen to exert an anti-inflammatory activity is higher than the analgesic dose, i.e., in the order of 800 to 1200 mg. per day. At 800 mg. per day, indoprofen is effective in the treatment of osteoarthritis. At this dose gastrointestinal ulceration and other side effects are minimal. At 1200 mg. per day, indoprofen is effective in the treatment of rheumatoid arthritis, but the incidence of gastrointestinal ulceration and other side effects are recognized. Based upon clinical studies, up to 800 mg. per day is classified as a safe dose, however, above 800 mg., especially 1200 mg., per day has not been shown to be safe for prolonged therapy.

The clinical studies show that as the indoprofen dose is increased, the plasma peak height and the bioavailability as measured by total area under the plasma curve increases in a linear fashion. For instance, humans given 100 mg. and 200 mg. indoprofen showed peak heights of 8.3±1.6 µg per ml. and 15.1±4.6 µg per ml., respectively. Also, the total area under the plasma curve for the corresponding doses were 28.7±7.6 µg ml. per hr. and 56.2±15.1 µg ml. per hr., respectively.

The study in mice reported in Table I shows indoprofen given as the pure drug and in microencapsulated form have equivalent bioavailability. For instance, with the pure drug, the area under the plasma curve can be calculated as 24.5 µg ml. per hr.; whereas, when microencapsulated, it can be calculated as 23.3 µg ml. per hr. However, note the plasma peak height with the pure drug is 2.5 µg per ml.; whereas when microencapsulated, it is only 1.1 µg per ml. In other words, the peak height with the pure drug is two times that of the microencapsulated drug.

It has now been found that the action of indoprofen can be prolonged up to eight-fold if it is microencapsulated by certain specific procedures and can even be further prolonged by compressing the microcapsules into tablets. In accordance with this invention sustained release idoprofen tablets are produced by encapsulating micro-particles of indoprofen in a solid protective coating of a cellulose ether and then compressing the microcapsules into tablets.

A microencapsulated formulation for indoprofen has now been discovered which can be used safely at its effective anti-inflammatory dose for the treatment of both osteoarthritis and rheumatoid arthritis in humans. Because indoprofen given in the form of pure drug and microencapsulated form are bioequivalent, but the plasma peak height obtained from the pure drug is two times that of microencapsulated form, it is now possible to use indoprofen at its effective doses of 800 and 1200 mg. per day without encountering the incidence of systemic side effects.

Also, by microencapsulation there now is a delivery system by which the release of indoprofen in the gastrointestinal tract can be controlled, thereby preventing localized high concentrations. Indoprofen, like other drugs in this category, is a weak acid and is unionized in the acidic pH of the stomach and thus poorly soluble. The cellulose ether coating of the microencapsulation process forms a gel in the stomach pH from which indoprofen diffuses slowly, minimizing the possibility of high local concentration.

It is important that the particle size of indoprofen be below 20 microns and the nominal coating thickness by microencapsulation be approximately 50–250 microns to adequately provide the acceptable properties necessary to minimize the side effects associated with 80 and 1200 mg. of indoprofen which is indicated in the treatment of osteoarthritis and rheumatoid arthritis.

The specific process used to microencapsulate the microparticles of indoprofen comprises warming and then cooling the particles while dispersed in specific immiscible liquids, one of which is a solvent for the cellulose ether when warm but not when cool. In particular, the process requires the use of three immiscible phases:

(1) a liquid mixture of which a major part by volume is a low-viscosity liquid which acts as a solvent for the cellulose ether at warm temperatures and a minor part by volume of a polymer which acts to force the cellulose ether out of solution at cool temperature;

(2) A cellulose ether which will form a solid protective coating, is incompatible with the polymer of (1) but is soluble in the low-viscosity liquid solvent (1) at warm temperature, and which with the solvent forms a separate phase (the cellulose ether being used in an amount such that the warm solution has a viscosity of from about 4,000 to about 10,000 centipoises and may by agitation be dispersed as minute liquid entities ready to coat the indoprofen particles); and (3) micro-particles of indoprofen, below 20 microns, which are immiscible with (1) or (2) but are wettable by the warm solution of cellulose ether in the low-viscosity solvent.

Only those cellulose ethers which conform to certain specific criteria may be used to prepare the microencapsulated indoprofen of this invention. First, the cellulose ether must be capable, when in warm solution, of wetting the indoprofen particles so as to form a complete liquid shield around the particles which when cooled solidify without retention of the solvent. Second, the cellulose ether must be soluble when warmed in the low-viscosity liquid solvent, capable of forming a separate phase in the warm solvent in the presence of the polymer and insoluble in the cool solvent in the presence of the polymer. Typical of the cellulose ethers which fit the above criteria are ethyl cellulose and ethyl hydroxyethyl cellulose.

The liquid mixture used to prepare the microencapsulated indoprofen of this invention will contain two essential ingredients: (1) a major part of a low-viscosity liquid, which will act as a solvent for the cellulose ether at warm temperatures and form a separate phase containing the cellulose ether and (2) a minor part of a polymeric ingredient with which the cellulose ether is immiscible and which forces the cellulose ether out of solution at cool temperatures. Typical of the low-viscosity liquids which can be used are cyclohexane and toluene. Typical of the polymeric ingredients are polybutadiene and butyl rubber.

Various amounts of the indoprofen, cellulose ether an liquid mixture can be used in the preparation of the encapsulated indoprofen of this invention, depending upon the specific ingredients used and the thickness of the encapsulating coating desired. In general, however, the liquid mixture will constitute at least 70% by weight of the three immiscible phases, of which the low viscosity liquid will constitute the major part. The cellulose ether will be present in an amount such that the warm solution has a viscosity of from about 4,000 to about 10,000 centiposes. The indoprofen which constitutes the remaining immiscible phase will be present in the form of minute particles smaller than 50 microns, most preferably smaller than 20 microns.

The temperatures used during the steps of the preparation of the encapsulated indoprofen will vary depending upon the specific liquid mixture and cellulose ether used. In general, however, the three immiscible phases will be heated to a temperature in the range of from about 50° C. to about 90° C. and then cooled to about room temperature or slightly above room temperature.

The compression of the microencapsulated indoprofen into tablets will be carried out in accordance with well known tableting procedures.

Besides the above essential ingredients; other conventional tableting ingredients can also be included in the tablets. Accordingly, antioxidants such as ascorbic acid or sodium metabisulfite; lubricants such as talc, magnesium stearate or sodium lauryl sulfate; fillers such as lactose calcium diphosphate; and colorants may be added if desired. However, it should be understood the inclusion of microencapsulated indoprofen constitutes the critical feature of this invention.

It may also be desirable to include other medicaments in the tablets, such as other analgesics, antihistamines, hypoglycemics, antidepressants, bronchodilators, sedatives, decongestants, antispasmodics, etc.

Th following examples will serve to illustrate the invention; however, they should not be considered as limiting the scope thereof. All parts and percentages are by weight unless indicated otherwise.

EXAMPLE 1

This example illustrates the microencapsulation of indoprofen in ethyl cellulose.

The following ingredients are used:
(1) cyclohexane as the low viscosity liquid,
(2) butyl rubber having a viscosity of 60-75 "Mooney" 8 minute reading at 212° F., as the polymer component of the liquid mixture,
(3) ethyl cellulose having an ethoxyl content of approximately 48.5% by weight, and a viscosity of 90-94 centipoises as a 5% by weight solution in a 20% alcohol/toluene solvent, as the cellulose ether, and
(4) indoprofen particles having a size of less than 20 microns.

To 200 parts of a 3% solution of the above described butyl rubber in cyclohexane is added 4 parts of the above described ethyl cellulose and 48 parts of the above described indoprofen particles and the whole heated to 80° C. with agitation sufficient to produce separate phase droplets of ethyl cellulose in cyclohexane of approximately 2 microns average drop size. The droplets coat the indoprofen particles. The dispersion is then slowly cooled to room temperature with continued agitation. During the cooling the ethyl cellulose deposits as a rigid coating on the indoprofen particles. The resulting microencapsulated indoprofen is removed by centrifuging and dried. The microencapsulated product is suitable for placing in capsules or compressing into tablets either alone or in combination with conventional pharmaceutical ingredients.

EXAMPLE 2

This example illustrates the difference in indoprofen plasma level over a time period between mice given pure indoprofen and mice given microencapsulated indoprofen.

Plasma levels of indoprofen are determined in adult mice (22–25 g.) following oral gavage of either pure drug or microencapsulated drug. Drugs are administered at 1% of the body weight. Each treatment group in a single experiment contains four animals and the data is pooled for evaluation. Animals are sacrificed by decapitation. Blood from each treatment group is collected and pooled in heparinized tubes. Plasma is collected and frozen for assay of indoprofen concentration. Plasma indoprofen concentration is determined by high pressure liquid chromatography fitted with a UV detector; concentration is determined at max. 284 nm.

The results of the experiments are shown in Table I.

TABLE I

| Plasma Level ($\mu$g/ml) of Indoprofen in Mice, Administered Orally as a Suspension* Mean + Standard Error | | |
|---|---|---|
| Time, hours | Pure Drug | Microencapsulated |
| 2 | 2.49 ± 0.45 | 1.10 ± 0.39 |

TABLE I-continued

Plasma Level (μg/ml) of Indoprofen in Mice,
Administered Orally as a Suspension*
Mean ± Standard Error

| Time, hours | Pure Drug | Microencapsulated |
|---|---|---|
| 4 | 1.62 ± 0.15 | 1.03 ± 0.24 |
| 8 | 0.89 ± 0.24 | 0.89 ± 0.16 |
| 16 | 0.49 ± 0.17 | 0.57 ± 0.29 |
| 32 | 0.43 ± 0.0 | 0.66 ± 0.47 |
| $K_e$, hr.$^{-1a}$ | 0.1276 | 0.0155 |
| $t_{\frac{1}{2}}$, hr.$^b$ | 5.4 | 44.7 |

*Aqueous suspension containing 0.5% methylcellulose and 0.06% surface active agent.
$^a$The apparent rate of elimination, $K_e$ is calculated using a one compartment open model system as described by J. G. Wagner Biopharmaceutics and Relevant Pharmacokinetics, page 180, Hamilton Press (1971)
$^b$The plasma half-life, $t_{\frac{1}{2}}$ is determined using the relationship $t_{\frac{1}{2}} = \frac{0.693}{K_e}$ It can be seen from the above that the encapsulated drug has a plasma half-life eight times longer than the unencapsulated drug.

EXAMPLE 3

This example illustrates the dissolution rate of the microencapsulated indoprofen of this invention as compared with the non-encapsulated drug.

The in vitro dissolution analysis is done using the United States Pharmacopeia apparatus at 100 rpm (The United States Pharmacopeia, 19th rev., page 651, 1975, Mack Publishing Co.).

Capsules are prepared by placing 50 mg. of pure indoprofen or microencapsulated product containing 50 mg. of indoprofen into hard gelatin capsule shells, size No. 2. Tablets are prepared by compressing microencapsulated product contaning 100 mg. of indoprofen on a tablet machine using 9/32" flat, face tooling. Each capsule and tablet is placed in a rotating basket and immersed in 900 ml. of simulated intestinal fluid (no pancreatin). At 10, 20, 30, 60, 120 and 180 minutes, 5 ml. samples are withdrawn, filtered through a 0.6 micron membrane filter and assayed for absorbance in a UV spectrophotometer at λ max. 284 nm. The percent of indoprofen dissolved is calculated, each value being an average of two analyses. The results of the analyses are shown in Table II.

TABLE II

| Product | Percent Dissolved (Minutes) | | | | | |
|---|---|---|---|---|---|---|
| | 10 | 20 | 30 | 60 | 120 | 180 |
| Pure drug capsule | 36.7 | 92.8 | 96.3 | 97.2 | 96.3 | — |
| Microencapsulated capsule | 4.2 | 9.3 | 8.9 | 17.3 | 28.6 | — |
| Microencapsulated tablet | 2.3 | 3.5 | 4.0 | 5.7 | 10.0 | 11.6 |

EXAMPLE 4

This example illustrates the use of microencapsulated indoprofen in prolonged release formulations containing other medicaments.

In each case the ingredients are blended in a twin shell blender for 5 minutes and then compressed into tablets. Formulations 1 and 2 are compressed into 530 mg. tablets on a tablet machine using ⅜" flat face tablet tooling. Formulations 3-5 are compressed into 330 mg. tablets on a tablet machine using 7/16" flat face tablet tooling. The ingredients are set forth below:

| | Mg. per Tablet | % |
|---|---|---|
| Formulation 1 | | |
| Microencapsulated indoprofen | 118.0 | 22.3 |
| Aspirin, USP | 325.0 | 61.3 |
| Lactose Fast flo, USP | 79.5 | 15.0 |
| Magnesium stearate, USP | 7.5 | 1.4 |
| | 530.0 | 100.0 |
| Formulation 2 | | |
| Microencapsulated indoprofen | 118.0 | 22.3 |
| Acetaminophen, USP | 325.0 | 61.3 |
| Lactose Fast flo, USP | 79.5 | 15.0 |
| Magnesium stearate, USP | 7.5 | 1.4 |
| | 530.0 | 100.0 |
| Formulation 3 | | |
| Microencapsulated indoprofen | 118.0 | 35.8 |
| Indoprofen, Pure drug | 50.0 | 15.1 |
| Lactose Fast flo, USP | 157.0 | 47.6 |
| Magnesium stearate, USP | 5.0 | 1.5 |
| | 330.0 | 100.0 |
| Formulation 4 | | |
| Microencapsulated indoprofen | 118.0 | 35.8 |
| Propoxyphene hydrochloride USP | 65.0 | 19.7 |
| Lactose Fast flo, USP | 142.5 | 43.2 |
| Magnesium stearate, USP | 4.5 | 1.3 |
| | 330.0 | 100.0 |
| Formulation 5 | | |
| Microencapsulated indoprofen | 118.0 | 35.8 |
| Phenobarbitol Sodium, USP | 15.0 | 4.5 |
| Lactose Fast flo, USP | 192.5 | 58.3 |
| Magnesium stearate, USP | 4.5 | 1.3 |
| | 330.0 | 100.0 |

What we claim and desire to protect by Letters Patent is:

1. In the method of administering the anti-inflammatory and analgesic drug indoprofen gastro-intestinally not only in order to obtain an analgesic effect at a dose in the order of 100 to 600 mg. per day, within which dosage regimen indoprofen exhibits its maximum analgesic effect and has minimal or negligible side effects, but also to exert an anti-inflammatory activity at a dose in the order of 800 mg. per day, within which it is effective in the treatment of osteoarthritis with minimal gastrointestinal ulceration and other side effects, up to 1200 mg. per day, wherein indoprofen is effective in the treatment of rheumatoid arthritis but with recognized incidence of gastro-intestinal ulceration and other side effects, and wherein clinical studies show that as the indoprofen dose is increased, the plasma peak height and the bioavailability, as measured by total area under the plasma curve increases in a linear fashion, and wherein study in mice shows indoprofen given as the pure drug and in microencapsulated form have equivalent bioavailablity, the improvement wherein the action of indoprofen can be prolonged up to about eight-fold if it is microencapsulated and can even be further prolonged by compressing the micro-capsules into tablets, comprising administering a microencapsulate formulation for indoprofen which can be used safely at its effective anti-inflammatory dose for the treatment of both osteoarthritis and rheumatoid arthritis in humans, and wherein the release of indoprofen in the gastro-intestinal tract can be controlled, thereby preventing localized high concentrations, said composition comprising tablets of microencapsulated indoprofen prepared by (1) heating a dispersion of microparticles below 20 microns of indoprofen in a liquid mixture with a cellulose ether, said liquid mixture comprising a major part by volume of a low-viscosity liquid which is a solvent for the cellulose ether and a minor part by volume of a polymer which is incompatible with the cellulose ether, said cellulose ether being soluble in the low-viscosity liquid part of the liquid mixture when the mixture is heated to form a separate phase, said cellulose ether being present in such amount that the warm solution of it has a viscosity of 4,000 to 10,000 centipoises and may be broken up as tiny liquid droplets by agitation, said microparticles of indoprofen and cellulose ether comprising less than 30% by weight of the dispersion, (2) cooling the heated dispersion with agitation to a temperature at which the cellulose ether forms a solid protective coating of about 50 to 250 microns thickness on each microparticle of indprofen, (3) recovering the microencapsulated indoprofen and (4) compressing the microencapsulated indoprofen into tablets.

2. The method of claim 1 where the cellulose ether is ethyl cellulose.

3. The method of claim 1 where the low-viscosity liquid is cyclohexane.

4. The method of claim 1 where the polymer is butyl rubber.

5. In the method of administering the anti-inflammatory and analgesic drug indoprofen gastro-intestinally not only in order to obtain an analgesic effect at a dose in the order of 100 to 600 mg. per day, within which dosage regimen indoprofen exhibits its maximum analgesic effect and has minimal or negligible side effects, but also to exert an anti-inflammatory activity at a dose in the order of 800 mg. per day, within which it is effective in the treatment of osteoarthritis with minimal gastrointestinal ulceration and other side effects, up to 1200 mg. per day, wherein indoprofen is effective in the treatment of rheumatoid arthritis but with recognized incidence of gastro-intestinal ulceration and other side effects, and wherein clinical studies show that as the indoprofen dose is increased, the plasma peak height and the bioavailability, as measured by total area under the plasma curve increases in a linear fashion, and wherein study in mice shows indoprofen given as the pure drug and in microencapsulated form having equivalent bioavailability, the improvement wherein the action of indoprofen can be prolonged up to about eightfold if it is microencapsulated and can even be further prolonged by comprising the micro-capsules into tablets, comprising administering a microencapsulate formulation for indoprofen which can be used safely at its effective anti-inflammatory dose for the treatment of both osteoarthritis and rheumatoid arthritis in humans, and wherein the release of indoprofen in the gastro-intestinal tract can be controlled, thereby preventing localized high concentrations, said composition comprising tablets of microencapsulated indoprofen prepared by (1) heating a dispersion of microparticles below 20 microns of indoprofen in a liquid mixture with ethyl cellulose, said liquid mixture comprising a major part by volume of cyclohexane and a minor part by volume of butyl rubber, said ethyl cellulose being soluble in the cyclhexane part of the liquid mixture when the mixture is heated to form a separate phase, said ethyl cellulose being present in such amount that the warm solution of it has a viscosity of 4,000 to 10,000 centipoises and may be broken up as tiny liquid droplets by agitation, said microparticles of indoprofen and ethyl cellulose comprising less than 30% by weight of the dispersion, (2) cooling the heated dispersion with agitation to a temperature at which the ethyl cellulose forms a solid protective coating of about 50 to 250 microns thickness on each microparticle of indoprofen, (3) recovering the microencapsulated indoprofen, and (4) compressing the microencapsulated indoprofen into tablets.

6. The method of claim 5 where other medicaments are present in the tablet.

7. The method of claim 6 where the other medicament is aspirin.

8. The method of claim 6 where the other medicament is propoxyphene hydrochloride.

9. The method of claim 6 where the other medicament is pure indoprofen.

10. The method of claim 6 where the other medicament is acetaminophen.

11. The method of claim 6 where the other medicament is phenobarbitol.

* * * * *